United States Patent
De Man et al.

(10) Patent No.: US 8,155,265 B2
(45) Date of Patent: Apr. 10, 2012

(54) ASYMMETRIC DE-POPULATED DETECTOR FOR COMPUTED TOMOGRAPHY AND METHOD OF MAKING SAME

(75) Inventors: Bruno Kristiaan Bernard De Man, Clifton Park, NY (US); Abdelaziz Ikhlef, Waukesha, WI (US); Jiang Hsieh, Brookfield, WI (US); Jeffrey Alan Kautzer, Pewaukee, WI (US); Robert F. Senzig, Germantown, WI (US); Paavana Sainath, Oconomowoc, WI (US); Xiaoye Wu, Rexford, NY (US); Jed Douglas Pack, Glenville, NY (US)

(73) Assignee: General Electric Company, Schnectady, NY (US)

( * ) Notice: Subject to any disclaimer, the term of this patent is extended or adjusted under 35 U.S.C. 154(b) by 138 days.

(21) Appl. No.: 12/837,035

(22) Filed: Jul. 15, 2010

(65) Prior Publication Data
US 2012/0014502 A1   Jan. 19, 2012

(51) Int. Cl.
*A61B 6/03* (2006.01)
(52) U.S. Cl. ........................................... 378/19
(58) Field of Classification Search ............... 378/4, 15, 378/19, 62, 98.8; 250/370, 370.11, 370.15; 29/592.1
See application file for complete search history.

(56) References Cited

U.S. PATENT DOCUMENTS

| | | | |
|---|---|---|---|
| 6,700,948 B2 | 3/2004 | Hoffman | |
| 6,979,826 B2 | 12/2005 | Ikhlef | |
| 7,062,009 B2 * | 6/2006 | Karimi et al. | 378/19 |
| 7,260,174 B2 | 8/2007 | Hoffman et al. | |
| 2001/0028697 A1 * | 10/2001 | Nahaliel et al. | 378/19 |
| 2003/0123604 A1 * | 7/2003 | Edic et al. | 378/19 |
| 2010/0215142 A1 * | 8/2010 | Dafni et al. | 378/19 |

* cited by examiner

*Primary Examiner* — Irakli Kiknadze
(74) *Attorney, Agent, or Firm* — Ziolkowski Patent Solutions Group, SC (57) ABSTRACT

A computed tomography (CT) detector array includes a central region substantially symmetric about a central axis thereof and includes a first plurality of x-ray detector cells configured to acquire CT data from a first number of detector rows during a scan, wherein the central axis is in a channel direction of the CT detector array and transverse to a slice direction of the CT detector array. A first wing is coupled to a first side of the central region, and a second wing is coupled to a second side of the central region opposite the first side. The first and second wings include respective second and third pluralities of x-ray detector cells and are each configured to acquire CT data from a number of detector rows that is less than the first number of detector rows. The CT detector array is asymmetric about the central axis of the central region.

20 Claims, 5 Drawing Sheets

ASYMMETRIC DE-POPULATED DETECTOR FOR COMPUTED TOMOGRAPHY AND METHOD OF MAKING SAME

BACKGROUND OF THE INVENTION

Embodiments of the invention relate generally to diagnostic imaging and, more particularly, to an apparatus and method of detecting x-rays.

Typically, in x-ray systems, such as computed tomography (CT) imaging systems, an x-ray source emits a fan-shaped or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces an electrical signal indicative of the attenuated beam received by each detector element. The electrical signals are transmitted to a data processing system for analysis, which ultimately produces an image.

Generally, the x-ray source and the detector array are rotated about a gantry within an imaging plane and around the subject. X-ray sources typically include x-ray tubes, which emit the x-ray beam at a focal point. X-ray detectors also typically include an anti-scatter grid (sometimes called post-patient collimator) for eliminating scattered x-rays arriving at the detector, a scintillator for converting x-rays to light energy, and photodiodes for receiving the light energy from the adjacent scintillator and producing electrical signals therefrom. Typically, each scintillator element of a scintillator array converts x-rays to light energy, which is optically guided to a photodiode adjacent thereto. Each photodiode detects the light energy and generates a corresponding electrical signal. The outputs of the photodiodes are then transmitted to the data processing system for image reconstruction.

Current CT detectors generally use detectors such as scintillation crystal/photodiode arrays, where the scintillation crystal absorbs x-rays and converts the absorbed energy into visible light. These arrays are often based on front-illuminated photodiodes. However, for products where the number of detector rows is beyond 64, the designs are generally based on back-illuminated photodiodes.

A development of multi-slice CT systems has led the market to new applications in general and to cardiac and perfusion imaging in particular. A goal and/or desire of many clinicians is to image a heart within one gantry rotation (or within a half-scan or half a gantry rotation) and with improved temporal resolution. To address such goals or desires, detectors having a large coverage (e.g., system coverage up to 160 mm or more at iso-center) have been investigated and developed. Such detectors generally have a large number of detector rows (e.g., 256 rows or more) and are correspondingly capable of acquiring data corresponding to a large number of slices (e.g., 256 slices or more) during one scan or gantry rotation. It is noted, however, that detector costs generally increase as its number of detector rows increase.

Not all applications, however, greatly benefit from high-detector-row-count acquisitions such as 256 or more detector-row-acquisitions. For example, many conventional types of CT imaging do not require the increased coverage obtained by the use of 256-row detectors. As such, using a large row-count detector in many instances can be "overkill." To address this situation, technicians often employ more than one type of CT scanner. For example, when large coverage is needed, a technician may employ a 256-detector-row CT scanner, and when large coverage is not need, a technician may employ a 64-detector-row CT scanner. The use of multiple types of CT scanners, however, can be cost prohibitive because of the costs associated with purchasing multiple CT scanners.

It would therefore be beneficial to design a cost effective system including an x-ray detector capable of varying detector-row number.

BRIEF DESCRIPTION OF THE INVENTION

According to an aspect of the invention, a computed tomography (CT) detector array includes a central region substantially symmetric about a central axis thereof and includes a first plurality of x-ray detector cells configured to acquire CT data from a first number of detector rows during a scan, wherein the central axis is in a channel direction of the CT detector array and transverse to a slice direction of the CT detector array. A first wing is coupled to a first side of the central region and includes a second plurality of x-ray detector cells configured to acquire CT data from a second number of detector rows during the scan, the second number of detector rows being less than the first number of detector rows. A second wing is coupled to a second side of the central region opposite the first side and comprising a third plurality of x-ray detector cells configured to acquire CT data with a third number of detector rows during the scan, the third number of detector rows being less than the first number of detector rows. The CT detector array is asymmetric about the central axis of the central region.

According to another aspect of the invention, a computed tomography (CT) detector array includes a central detecting region having a central axis substantially bisecting the central detecting region in a channel direction, wherein the central detecting region includes an end-to-end z-dimension in a slice direction. The CT detector array also includes a first detecting wing having a z-dimension in the slice direction that is less than the z-dimension of the central detecting region and a second detecting wing having a z-dimension in the slice direction that is less than the z-dimension of the central detecting region. The first detecting wing is positioned along a first side of the central detecting region, and the second detecting wing is positioned along a second side of the central detecting region opposite the first side. The CT detector array is substantially asymmetric about the central axis substantially bisecting the central detecting region.

According to yet another aspect of the invention, a method of manufacturing a computed tomography (CT) detector array includes manufacturing a CT detector array such that the CT detector array is substantially asymmetric about a central axis of the CT detector array, wherein the central axis of the CT detector array is in a channel direction of the CT detector array and transverse to a slice direction of the CT detector array. Manufacturing the CT detector array includes assembling a central detecting region configured to acquire CT data for a first quantity of CT detector rows such that the central detecting region is substantially symmetric about the central axis of the CT detector array and assembling a first detecting wing such that the first detecting wing resides on a first side of the central detecting region, wherein the first detecting wing is configured to acquire CT data for a second quantity of CT detector rows less than the first quantity of CT detector rows. Manufacturing the CT detector array also includes assembling a second detecting wing such that the second detecting wing resides on a second side of the central detecting region opposite the first side, wherein the second detecting wing is configured to acquire CT data for a third quantity of CT detector rows less than the first quantity of CT detector rows.

These and other advantages and features will be more readily understood from the following detailed description of preferred embodiments of the invention that is provided in connection with the accompanying drawings.

DETAILED DESCRIPTION

Embodiments of the invention support the acquisition of both anatomical detail for medical CT as well as structural detail for components within objects such as luggage.

The operating environment of the invention is described with respect to a computed tomography (CT) system. Moreover, the invention will be described with respect to the detection and conversion of x-rays. However, one skilled in the art will further appreciate that the invention is equally applicable for the detection and conversion of other high frequency electromagnetic energy. The invention will also be described with respect to a "third generation" CT scanner, but is equally applicable with other CT systems.

Figure 1:
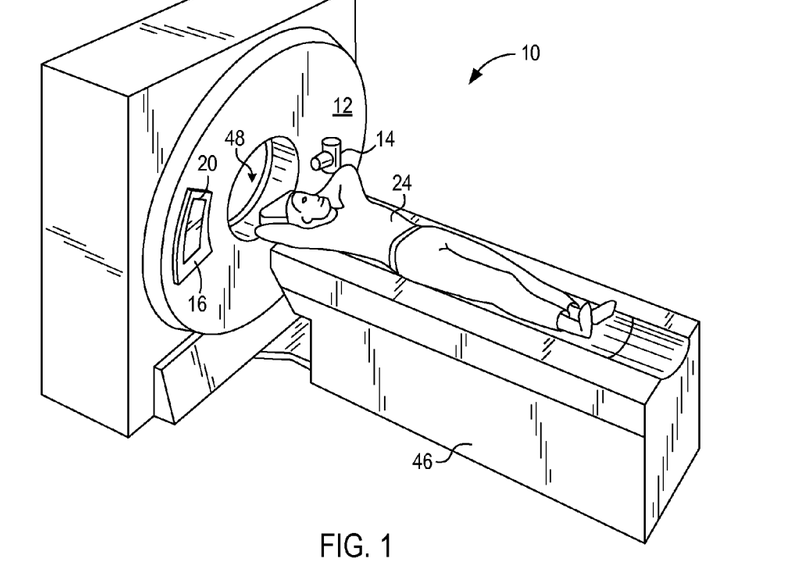
FIG. 1 is a pictorial view of a CT imaging system.
Figure 2:
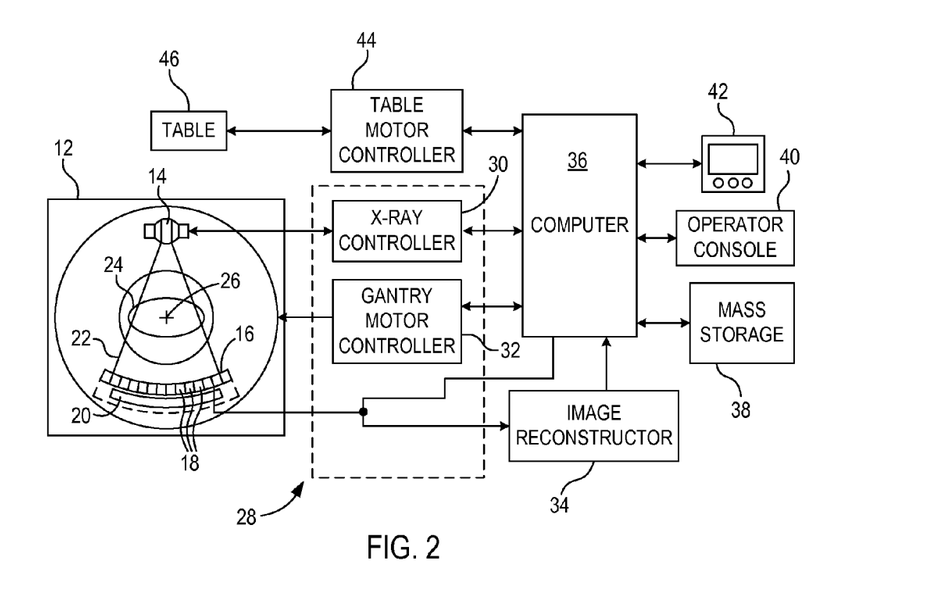
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector array or collimator 16 on the opposite side of the gantry 12. Referring now to FIG. 2, detector array 16 is formed by a plurality of modules 18 and a data acquisition system (DAS) 20. The plurality of modules 18 sense the projected x-rays 22 that pass through a subject 24, and DAS 20 converts the data to digital signals for subsequent processing. Each module 18 produces multiple analog electrical signals that represent intensities of an impinging x-ray beam and hence the attenuated beam as it passes through subject 24. Further details regarding detector array 16 will be set forth in detail below with respect to FIGS. 3-12.

During a scan to acquire x-ray projection data, gantry 12 and the components mounted thereon rotate about a center of rotation 26. Rotation of gantry 12 and the operation of x-ray source 14 are governed by a control mechanism 28 of CT system 10. Control mechanism 28 includes an x-ray controller 30 that provides power and timing signals to an x-ray source 14 and a gantry motor controller 32 that controls the rotational speed and position of gantry 12. An image reconstructor 34 receives sampled and digitized x-ray data from DAS 20 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 20, x-ray controller 30 and gantry motor controller 32. In addition, computer 36 operates a table motor controller 44 which controls a motorized table 46 to position subject 24 and gantry 12. Particularly, table 46 moves subject 24 through a gantry opening 48 of FIG. 1 in whole or in part.

Figure 3:
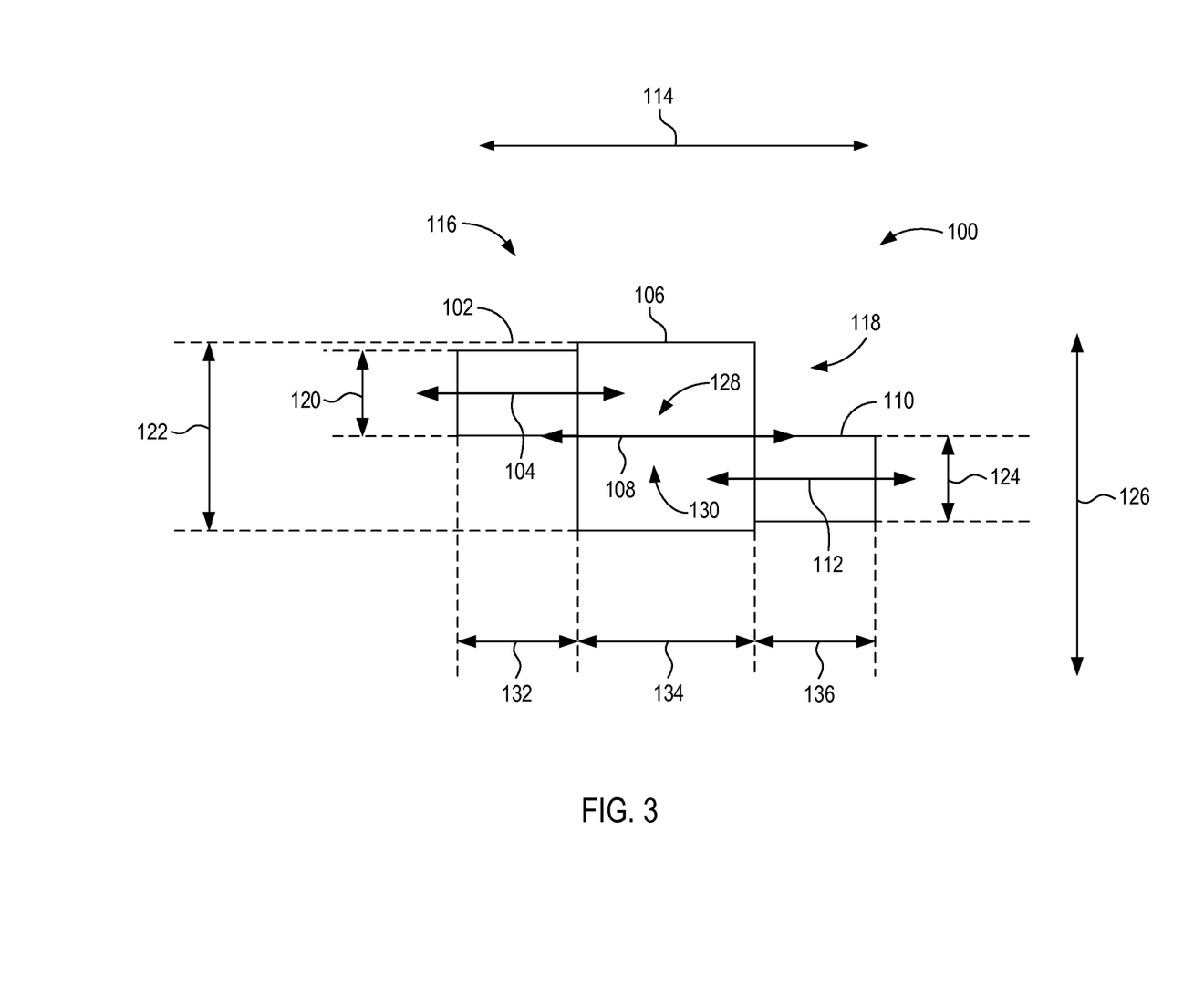
FIGS. 3-9 are block diagrams of detector arrays according to various embodiments of the invention.

Referring to FIG. 3, a block diagram of a detector array 100 is shown according to an embodiment of the invention. Detector array 100 includes a first detecting wing 102 having a central axis 104 passing therethrough, a central detecting region 106 having a central axis 108 passing therethrough, and a second detecting wing 110 having a central axis 112 passing therethrough. As depicted, central axis 108 substantially bisects central detecting region 106 and proceeds in a channel direction 114 (i.e., an x-direction).

First detecting wing 102 is on a first side 116 of central detecting region 106, and second detecting wing 110 is on a second side 118, opposite first side 116, of central detecting region 106.

Each of first detecting wing 102, central detecting region 106, and second detecting wing 110 has a detector-row number or an end-to-end z-dimension 120, 122, 124, respectively, in a z-direction 126 (i.e., slice direction). According to embodiments of the invention, detector-row number 122 of central detecting region 106 is greater than each of detector-row numbers 120, 124 of first and second detecting wings 102, 104, respectively. As depicted in the embodiment of FIG. 3, detector-row numbers 120, 124 of first and second wings 102, 104, respectively, are substantially equal. It is contemplated, however, that detector-row number 120 need not be equal to detector-row number 124. In other words, detector-row number 120 of first detecting wing 102 may be different than detector-row number 124 of second detecting wing 104.

According to an embodiment, detector-row number 122 of central detecting region 106 is substantially equivalent to 256 rows, and detector-row number 120, 124 of first and second detecting wings 102, 104, respectively, are each substantially equivalent to 64 rows. It is noted that these exemplary detector-row numbers (e.g., 256 detector-row number and 64 detector-row number) are not limited to 64 rows and that detector-row numbers equivalent to more or less than 256 rows and 64 rows are contemplated.

It is noted that the terms "first" and "second" as set forth herein are merely used to distinguish one feature or aspect of the invention from another (e.g., first detecting wing 102 versus second detecting wing 110). As such, the terms "first" and "second" are not intended to imply a sequential spatial or temporal relationship. For example, one could, alternatively, view wing 110 as a first wing and wing 102 as a second wing. Similarly, one could view side 118 as a first side and side 116 as a second side.

Referring to back to the present embodiment, though central axis 108 substantially bisects central detecting region 106, central axis 108 does not substantially bisect first and second detecting wings 102, 110. Rather, central axis 104 substantially bisects first detecting wing 102 and lies on a first side 128 of central axis 108 of central detecting region 106. Similarly, central axis 112 substantially bisects second detecting wing 110 and lies on a second side 130, opposite first side 128, of central axis 108. As illustrated, central axes 104, 108, 112 are parallel to one another, but non-coincident.

According to an alternate embodiment, first detecting wing 102 may be positioned such that central axis 104 thereof lies on second side 130 of central axis 108 of central detecting region 106, and second detecting wing 110 may be positioned such that central axis 112 thereof lies on first side 128 of central axis 108.

As illustrated in FIG. 3, each region (i.e., first detecting wing 102, central detecting region 106, and second detecting wing 110) has a respective width dimension 132-136. According to the embodiment shown in FIG. 3, first wing width 132 and second wing width 136 are each less than central region width 134. It is contemplated, however, one or both of first and second wing widths 134, 136 may be greater than or equal to central region width 134. In addition, though first and second wing widths 132, 136 are substantially equal in the embodiment of FIG. 3, embodiments are envisioned where first and second wing widths 132, 136 are not substantially equal.

Embodiments of the invention include a CT detector (e.g., detector array 100) having a central detecting region, a first detecting wing on one side of the central detecting region, and a second detecting wing on an opposite side of the central detecting region. The CT detector array is configured such that at least one of the first or second detecting wings is asymmetric (i.e., not symmetric) about a central axis in the channel direction that substantially bisects the central region. In other words, the CT detector array is asymmetric about the substantially central bisecting axis of the central detecting region. Further, effective volumetric coverage in an axial scan mode can be increased. In addition, detector costs can be reduced, and the x-ray tube target angle can be reduced. Other exemplary embodiments of the invention are shown below in FIGS. 4-9.

Figure 4:
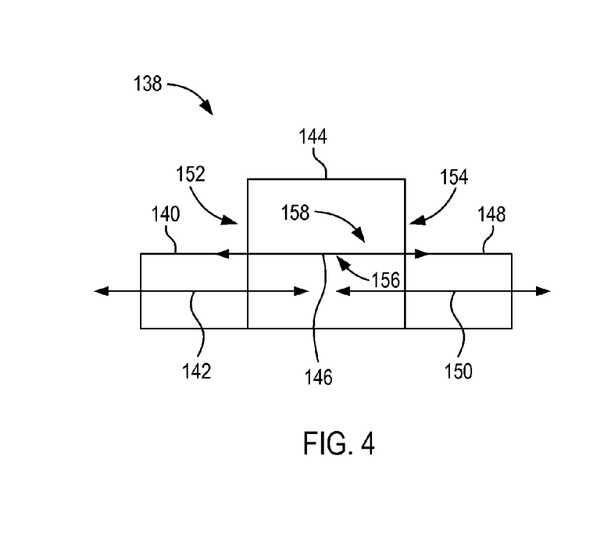

Referring now to FIG. 4, a detector array 138 is shown according to an embodiment of the invention. Detector array 138 includes a first detecting wing 140 having a central axis 142 passing therethrough, a central detecting region 144 having a central axis 146 passing therethrough, and a second detecting wing 148 having a central axis 150 passing therethrough. Central axis 142 substantially bisects first detecting wing 140, central axis 146 substantially bisects central detecting region 144, and central axis 150 substantially bisects second detecting wing 148. Further, first detecting wing 140 lies on a first side 152 of central detecting region 144, and second detecting wing 148 is on a second side 154, opposite first side 152, of central detecting region 144. Similar to the embodiment depicted in FIG. 3, though central detecting region 144 of FIG. 4 is substantially symmetric about central axis 146, detector array 138 is substantially asymmetric about central axis 146 of central detecting region 144.

According to the embodiment shown in FIG. 4, central axes 142, 150 of first and second wings 140, 148, respectively, each lie on a first side 156 of central axis 146 of central detecting region 144, where first side 156 is opposite a second side 158 of central axis 146. Further, each central axis 142, 150 is substantially parallel to central axis 146 of central detecting region 144. Though not shown, it is contemplated that in an alternate embodiment, first and second wings 140, 148 may be positioned such that central axes 142, 150 thereof lie on second side 158 of central axis 146 of central detecting region 144 rather than on first side 156 of central axis 146.

Figure 5:
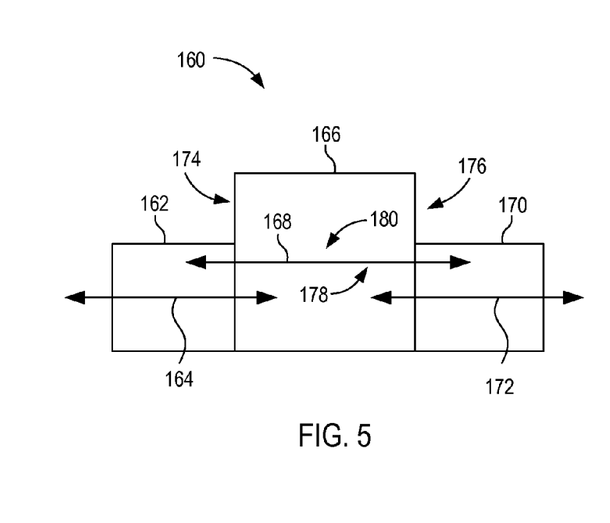

Referring now to FIG. 5, a block diagram of a CT detector array 160 is shown according to another embodiment of the invention. Detector array 160 includes a first detecting wing 162 having a central axis 164 passing therethrough, a central detecting region 166 having a central axis 168 passing therethrough, and a second detecting wing 170 having a central axis 172 passing therethrough. Central axis 164 substantially bisects first detecting wing 162, central axis 168 substantially bisects central detecting region 166, and central axis 172 substantially bisects second detecting wing 170. Further, first detecting wing 162 lies on a first side 174 of central detecting region 166, and second detecting wing 170 is on a second side 176, opposite first side 174, of central detecting region 166.

Similar to the embodiments depicted in FIGS. 3 and 4, though central detecting region 166 of FIG. 5 is substantially symmetric about central axis 168, detector array 160 is substantially asymmetric about central axis 168 of central detecting region 166.

According to the embodiment shown in FIG. 5, central axes 164, 172, of first and second wings 162, 170, respectively, each lie on a first side 178 of central axis 168 of central detecting region 166, where first side 178 is opposite a second side 180 of central axis 168. Further, each central axis 164, 172 is substantially parallel to central axis 168 of central detecting region 166. As shown in FIG. 5, a portion of both first and second detecting wings 162, 170 lies along central axis 168 of central detecting region 166. However, a majority of both first and second detecting wings 162, 170 reside on first side 178 of central axis 168.

Though FIG. 5 depicts central axis 164 and central axis 172 being coincident, it is contemplated that first and second detecting wings 162, 170 may be offset such that central axis 164 and central axis 172 are not coincident but are still parallel and on first side 178 of central axis 168.

Though not shown, it is contemplated that first and second detecting wings 162, 170 may be positioned such that central axes 164, 172 lie on second side 180 of central axis 168 of central detecting region 166 rather than on first side 178 of central axis 168.

Figure 6:
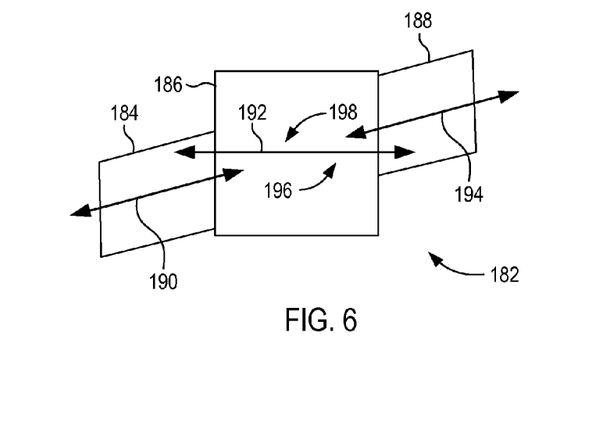

Referring now to FIG. 6, a configuration of a detector array 182 is shown according to another embodiment of the invention. Detector array 182 includes a first detecting wing 184, a central detecting region 186, and a second detecting wing 188. Each detecting region (i.e., first detecting wing 184, central detecting region 186, and second detecting wing 188) has a substantially bisecting central axis 190-194, respectively, therethrough. In the embodiment of FIG. 6, however, central axes 190, 194 of first and second detecting wings 184, 188, respectively, are substantially non-parallel with central axis 192 of central detecting region 186.

Similar to the embodiments depicted in FIGS. 3-5, though central detecting region 186 of FIG. 6 is substantially symmetric about central axis 192 of central detecting region, detector array 182 is substantially asymmetric about central axis 192 of central detecting region 186.

As shown in FIG. 6, a majority of first wing 184 lies on a first side 196 of central axis 192 of central region 186, and a majority of second detecting wing 188 lies on a second side 198, opposite first side 196, of central axis 192. Though not shown, it is contemplated that a majority of first wing 184 may lie on second side 198, rather than first side 196, and a majority of second detecting wing 188 may lie on first side 196 rather than second side 198. As illustrated in FIG. 6, central axes 190, 194 are substantially non-parallel with central axis 192 of central detecting region 186.

Further, though central axes 190, 194 are substantially parallel and coincident with each other according to the embodiment shown in FIG. 6, it is contemplated that central axis 190, 194 may be offset from each other (i.e., non-coincident) but still parallel with each other. It is also contemplated that central axes 190, 194 may be non-parallel with each other, while also being non-parallel with central axis 192 of central detecting region 186.

Figures 7, 8, 9:
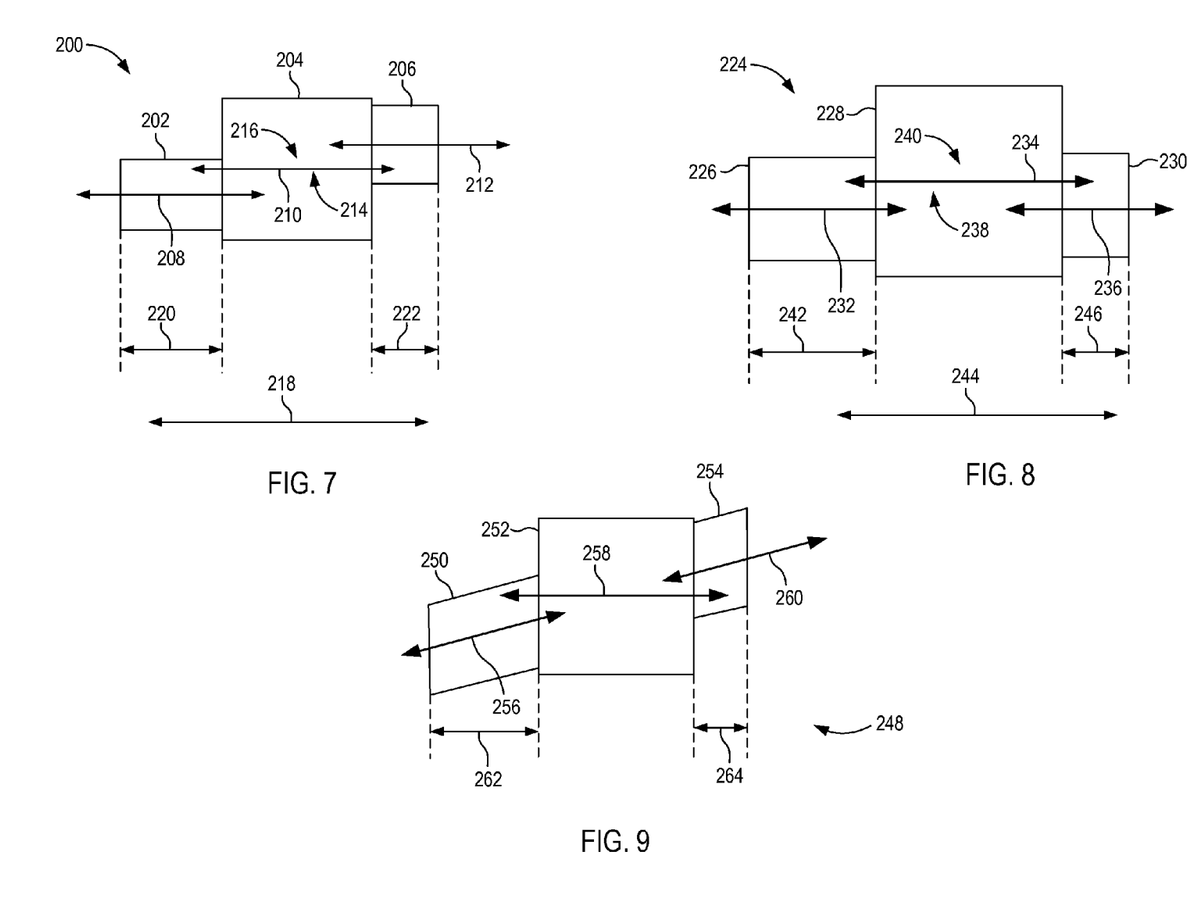

Referring to FIG. 7, a CT detector array 200 is shown according to another embodiment of the invention. As with the embodiments of FIGS. 3-6, the embodiment of FIG. 7 also depicts a first detecting wing 202, a central detecting region 204, and a second detecting wing 206, each having a substantially bisecting central axis 208-212, respectively. Similar to the embodiment of FIG. 3, central axes 208-212 of FIG. 7 are substantially parallel, but non-coincident with each other. In addition, though central detecting region 204 is substantially symmetric about central axis 210 of central detecting region 204, detector array 200 is substantially asymmetric about central axis 210 of central detecting region 204.

In contrast to the embodiment depicted in FIG. 3, central axis 210 of FIG. 7 passes through first and second detecting wings 202, 206. Though central axis 210 passes through first and second detecting wings 202, 206, a majority of first detecting wing 202 lies on a first side 214 of central axis 210 of central detecting region 204, and a majority of second detecting wing 206 lies on a second side 216, opposite first side 214, of central axis 210 of central detecting region 204.

Though not shown, it is contemplated that first wing 202 may be positioned such that central axis 208 thereof lies on second side 216 of central axis 210 and that second wing 206 may be positioned such that central axis 212 thereof lies on first side 214 of central axis 210.

According to embodiments of the invention, it is contemplated that first and second wings 202, 206 need not have the same dimensions in a channel direction 218 (i.e., an x-direction). FIG. 7 depicts an example of such an embodiment. As shown in FIG. 7, first detecting wing 202 has a first wing width 220 in x-direction 218, and second detecting wing 206 has a second wing width 222 in channel direction 218. Though, according to the embodiment of FIG. 7, first wing width 220 is larger than second wing width 222, it is contemplated that first wing width 220 may be less than or equal to second wing width 222.

Other exemplary embodiments illustrating a detector array having first and second wings of different dimensions are shown in FIGS. 8 and 9.

Referring to FIG. 8, a detector array 224 having a first detecting wing 226, a central detecting region 228, and a second detecting wing 230 is shown according to an embodiment of the invention. As with the embodiments of FIGS. 3-7, the embodiment of FIG. 8 also depicts first detecting wing 226, central detecting region 228, and second detecting wing 230 as each having a substantially bisecting central axis 232-236, respectively, passing therethrough. In addition, first and second detecting wings 226, 230 are positioned such that central axes 232, 236 thereof lie on a first side 238 of central axis 234 of central detecting region 228. It is contemplated, however, that first and second detecting wings 226, 230 may be positioned such that central axes 232, 236 thereof lie on a second side 240, opposite first side 238, of central axis 234 of central detecting region 228, rather than on first side 238.

Unlike the embodiment depicted in FIG. 5, first wing 226 of FIG. 8 has a first wing width 242 in an x-direction 244 (i.e., channel direction) different than a second wing width 246 of second detecting wing 230. In particular, first wing width 242 of first detecting wing 226 is greater than second wing width 246 of second detecting wing 230. Like FIG. 5, however, it is contemplated that first and second wing widths 242, 246 may be substantially equal. In addition, it is contemplated that first wing width 242 of first detecting wing 226 may be less than second wing width 246 of second detecting wing 230.

Referring to FIG. 9, a detector array 248 is shown according to another embodiment of the invention. Detector array 248 includes a first detecting wing 250, a central detecting region 252, and a second detecting wing 254, where each region (i.e., 250-254) has a respective central axis 256-260. Like the other embodiments of the invention, central detecting region 252 is substantially symmetric around its central axis 258 while detector array 248 is substantially asymmetric around central axis 258 of central detecting region 252.

Similar to the embodiment depicted in FIG. 6, central axis 256, 260 (FIG. 9) of first and second detecting wings 250, 254, respectively, are substantially parallel to each other and substantially non-parallel to central axis 258 of central detecting region 252.

However, unlike the embodiment of FIG. 6, first detecting wing 250 of FIG. 9 has a first wing width 262 that is greater than a second wing width 264 of second detecting wing 254. As with other embodiments of the invention, it is contemplated that second wing width 262 may be greater than or equal to first wing width 264 of first detecting wing 250.

It is contemplated that, according to embodiments of the invention, a CT detector array such as detector arrays 100, 138, 160, 182, 200, 224, 248, respectively of FIGS. 3-9, may employ one or more types of detecting cells. For example, each detecting wing and central detecting region of a detector array may employ the same type of detecting cells. According to an embodiment, each region (i.e., each detecting wing and central detecting region) may employ detecting cells having the same pixel density. According to other embodiments, each region may employ, for example, one of energy-integrating cells, photon counting cells, or energy discriminating cells. Other cell types, however, are contemplated.

It is also contemplated that the central detecting region of a CT detector array may employ a different type of detecting cell than one or more of the two detecting wings. For example, a central detecting region may employ detecting cells having a pixel density different than detecting cells employed by one or more of the two detecting wings. Similarly, the central detecting region may employ photon counting cells while one or more of the wings employ energy integrating detecting cells, or vice versa. Other CT detector arrays employing two or more detecting cells such as, for example, energy discriminating, photon counting, and energy integrating cells are also envisioned.

It is noted that one skilled in the art will readily appreciate that a CT detector is arc-shaped in a direction transverse to the z-direction (i.e., slice-direction) such that the trajectory of non-scattered impinging x-rays are orthogonal to the CT detector. Since FIGS. 3-9 are block diagrams, the arc shape of detector arrays 100, 138, 160, 182, 200, 224, 248 is not shown.

With regard to FIGS. 3-9, embodiments of the invention have been described in terms of three detection regions: two detecting wings and one central detecting region. It is noted, however, that detector arrays having more than three detecting regions are contemplated. For example, according to an embodiment (not shown), five detecting regions could be employed. In such an embodiment, there may be two outside detecting wings, a central detecting region, one intermediate region between the first detecting wing and the central detecting region, and another intermediate region between the second detecting wing and central detecting region. In such an instance, the two outside detecting wings may have a lower z-dimension height (i.e., wing height) than the central portion height, while the intermediate detecting regions may have a z-dimension height greater than or equal to the wing z-dimension height and less than or equal to the central portion z-dimension height. Other configurations having two detecting wings, a central detecting region, and additional detecting regions are contemplated.

According to embodiments of the invention, the central region of a CT detector array is substantially symmetric about a central axis thereof in the channel direction, while the entire array (e.g., the two detecting wings, the central region, and additional region(s)) is substantially asymmetric about the central axis of the central region.

Figure 10:
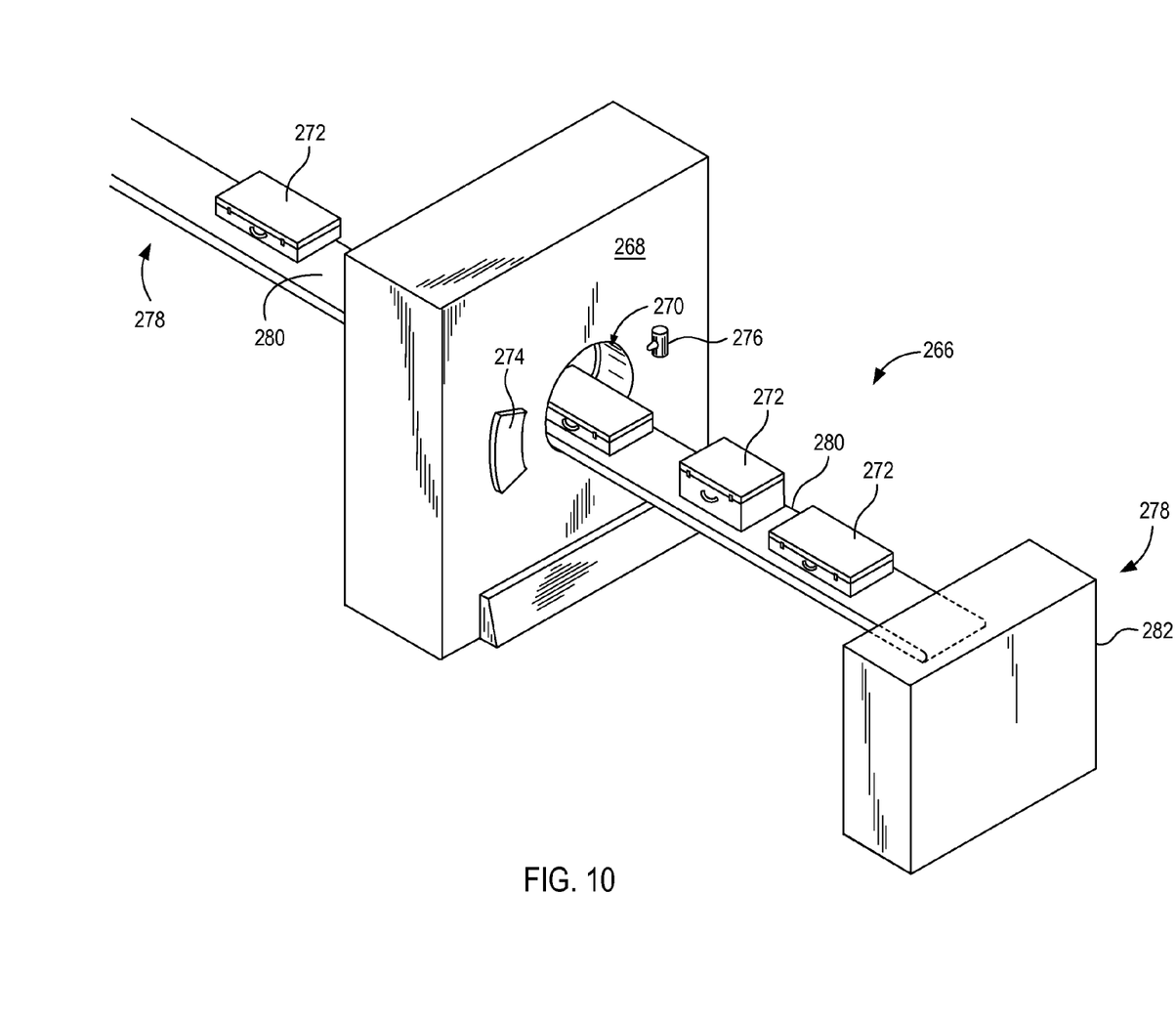
FIG. 10 is a pictorial view of a CT system for use with a non-invasive package inspection system according to an embodiment of the invention.

Referring now to FIG. 10, a pictorial view of an x-ray imaging system 266 for use with a non-invasive package inspection system is shown according to an embodiment of the invention. The x-ray system includes 266 a gantry 268 having an opening 270 therein through which a plurality of packages or pieces of baggage 272 may pass. The gantry 268 houses a detector assembly 274 that includes a CT detector array (e.g., detectors 100, 138, 160, 182, 200, 224, 248, respectively of FIGS. 3-9) and a high frequency electromagnetic energy source, such as an x-ray tube 276. A conveyor system 278 is also provided and includes a conveyor belt 280 supported by a structure 282 to automatically and continuously pass packages or baggage pieces 272 through opening 270 to be scanned. Objects 272 are fed through opening 270 by conveyor belt 280, imaging data is then acquired, and conveyor belt 280 removes the packages 272 from opening 270 in a controlled and continuous manner. As a result, postal inspectors, baggage handlers, and other security personnel may non-invasively inspect the contents of packages 272 for explosives, knives, guns, contraband, etc. One skilled in the art will recognize that gantry 268 may be stationary or rotatable. In the case of a rotatable gantry 268, system 266 may be configured to operate as a CT system for baggage scanning or other industrial or medical applications.

According to an embodiment of the invention, a computed tomography (CT) detector array includes a central region substantially symmetric about a central axis thereof and includes a first plurality of x-ray detector cells configured to acquire CT data from a first number of detector rows during a scan, wherein the central axis is in a channel direction of the CT detector array and transverse to a slice direction of the CT detector array. A first wing is coupled to a first side of the central region and includes a second plurality of x-ray detector cells configured to acquire CT data from a second number of detector rows during the scan, the second number of detector rows being less than the first number of detector rows. A second wing is coupled to a second side of the central region opposite the first side and comprising a third plurality of x-ray detector cells configured to acquire CT data with a third number of detector rows during the scan, the third number of detector rows being less than the first number of detector rows. The CT detector array is asymmetric about the central axis of the central region.

According to another embodiment of the invention, a computed tomography (CT) detector array includes a central detecting region having a central axis substantially bisecting the central detecting region in a channel direction, wherein the central detecting region includes an end-to-end z-dimension in a slice direction. The CT detector array also includes a first detecting wing having a z-dimension in the slice direction that is less than the z-dimension of the central detecting region and a second detecting wing having a z-dimension in the slice direction that is less than the z-dimension of the central detecting region. The first detecting wing is positioned along a first side of the central detecting region, and the second detecting wing is positioned along a second side of the central detecting region opposite the first side. The CT detector array is substantially asymmetric about the central axis substantially bisecting the central detecting region.

According to yet another embodiment of the invention, a method of manufacturing a computed tomography (CT) detector array includes manufacturing a CT detector array such that the CT detector array is substantially asymmetric about a central axis of the CT detector array, wherein the central axis of the CT detector array is in a channel direction of the CT detector array and transverse to a slice direction of the CT detector array. Manufacturing the CT detector array includes assembling a central detecting region configured to acquire CT data for a first quantity of CT detector rows such that the central detecting region is substantially symmetric about the central axis of the CT detector array and assembling a first detecting wing such that the first detecting wing resides on a first side of the central detecting region, wherein the first detecting wing is configured to acquire CT data for a second quantity of CT detector rows less than the first quantity of CT detector rows. Manufacturing the CT detector array also includes assembling a second detecting wing such that the second detecting wing resides on a second side of the central detecting region opposite the first side, wherein the second detecting wing is configured to acquire CT data for a third quantity of CT detector rows less than the first quantity of CT detector rows.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Furthermore, while single energy and dual-energy techniques are discussed or implied above, the invention encompasses approaches with more than two energies. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A computed tomography (CT) detector array comprising:
    a central region substantially symmetric about a central axis thereof and comprising a first plurality of x-ray detector cells configured to acquire CT data from a first number of detector rows during a scan, wherein the central axis is in a channel direction of the CT detector array and transverse to a slice direction of the CT detector array;
    a first wing coupled to a first side of the central region and comprising a second plurality of x-ray detector cells configured to acquire CT data from a second number of detector rows during the scan, the second number of detector rows being less than the first number of detector rows;
    a second wing coupled to a second side of the central region opposite the first side and comprising a third plurality of x-ray detector cells configured to acquire CT data with a third number of detector rows during the scan, the third number of detector rows being less than the first number of detector rows; and
    wherein the CT detector array is asymmetric about the central axis of the central region.

2. The CT detector array of claim 1 wherein:
    the first wing has a central axis that substantially bisects the first wing, and wherein the central axis of the first wing is substantially parallel with the central axis of the central region; and
    the second wing has a central axis that substantially bisects the second wing, and wherein the central axis of the second wing is substantially parallel with the central axis of the central region.

3. The CT detector array of claim 2 wherein the central axis of the first wing lies on a first side of the central axis of the central region, and wherein the central axis of the second wing lies on a second side of the central axis of the central region opposite the first side.

4. The CT detector array of claim 2 wherein the central axis of the central detecting region has a first side and a second side opposite the first side, and wherein the central axes of the first and second wings lie on the first side of the central axis of the central detecting region.

5. The CT detector array of claim 2 wherein the first wing has a first wing width in the channel direction and the second wing has a second wing width in the channel direction less than the first wing width.

6. The CT detector array of claim 1 wherein:
the first wing has a central axis substantially bisecting the first wing, and wherein the central axis of the first wing is substantially non-parallel with the central axis of the central region; and
the second wing has a central axis substantially bisecting the second wing, and wherein the central axis of the second wing is substantially non-parallel with the central axis of the central region.

7. The CT detector array of claim 6 wherein the first wing has a first wing width in the channel direction and the second wing has a second wing width in the channel direction less than the first wing width.

8. The CT detector array of claim 6 wherein at least a majority of the first wing lies on a first side of the central axis of the central region, and wherein at least a majority of the second wing lies on a second side of the central axis of the central region opposite the first side.

9. The CT detector array of claim 1 wherein the second and third number of detector rows are each substantially equivalent to 64 detector rows and the first number of slices is substantially equivalent to 256 detector rows.

10. The CT detector array of claim 1 wherein the second number of detector rows is substantially equivalent to the third number of detector rows.

11. The CT detector array of claim 1 wherein the second number of detector rows is less than the second number of detector rows.

12. A computed tomography (CT) detector array comprising:
a central detecting region having a central axis substantially bisecting the central detecting region in a channel direction, wherein the central detecting region comprises an end-to-end z-dimension in a slice direction;
a first detecting wing having a z-dimension in the slice direction that is less than the z-dimension of the central detecting region, the first detecting wing positioned along a first side of the central detecting region;
a second detecting wing having a z-dimension in the slice direction that is less than the z-dimension of the central detecting region, the second detecting wing positioned along a second side of the central detecting region opposite the first side; and
wherein the CT detector array is substantially asymmetric about the central axis substantially bisecting the central detecting region.

13. The CT detector array of claim 12 wherein the first detecting wing has a central axis substantially bisecting the first detecting wing, and wherein the second detecting wing has a central axis substantially bisecting the second detecting wing.

14. The CT detector array of claim 13 wherein the central axis of the first detecting wing and the central axis of the second detecting wing are non-parallel with the central axis of the central detecting region.

15. The CT detector array of claim 13 wherein the central axis of the first detecting wing lies on a first side of the central axis of the central detecting region and the central axis of the second detecting wing lies on a second side of the central axis of the central detecting region opposite the first side.

16. The CT detector array of claim 12 wherein each of the first and second detecting wings is configured to acquire CT data with 64 rows and the central detecting region is configured to acquire CT data with 256 rows.

17. A method of manufacturing a computed tomography (CT) detector array comprising:
manufacturing a CT detector array such that the CT detector array is substantially asymmetric about a central axis of the CT detector array, wherein the central axis of the CT detector array is in a channel direction of the CT detector array and transverse to a slice direction of the CT detector array, wherein manufacturing the CT detector array comprises:
assembling a central detecting region configured to acquire CT data for a first quantity of CT detector rows such that the central detecting region is substantially symmetric about the central axis of the CT detector array;
assembling a first detecting wing such that the first detecting wing resides on a first side of the central detecting region, wherein the first detecting wing is configured to acquire CT data for a second quantity of CT detector rows less than the first quantity of CT detector rows; and
assembling a second detecting wing such that the second detecting wing resides on a second side of the central detecting region opposite the first side, wherein the second detecting wing is configured to acquire CT data for a third quantity of CT detector rows less than the first quantity of CT detector rows.

18. The method of claim 17 wherein the second quantity of CT detector rows is substantially equivalent to the third quantity CT detector rows.

19. The method of claim 17 wherein manufacturing the CT detector array further comprises assembling the first and second detecting wings such that a majority of the first detecting wing resides on a first side of the central axis and a majority of the second detecting wing resides on a second side of the central axis opposite the first side.

20. The method of claim 17 wherein manufacturing the CT detector array further comprises assembling the first and second detecting wings such that a majority of the first and second wings reside on a first side of the central axis.

* * * * *